United States Patent [19]

Boyer

[11] 4,096,206

[45] Jun. 20, 1978

[54] FLAME-RETARDANT TRIAZINES

[75] Inventor: Nicodemus E. Boyer, Parkersburg, W. Va.

[73] Assignee: Borg-Warner Corporation, Chicago, Ill.

[21] Appl. No.: 656,469

[22] Filed: Feb. 9, 1976

[51] Int. Cl.² .................................................. C08K 5/34
[52] U.S. Cl. ........................ 260/880 R; 260/45.8 NT; 260/DIG. 24; 544/197; 544/219
[58] Field of Search ................... 260/45.8 NT, 880 R

[56] References Cited

U.S. PATENT DOCUMENTS

| | | | |
|---|---|---|---|
| 2,028,715 | 1/1936 | Hanson | 106/15 |
| 3,255,191 | 6/1966 | Dexter et al. | 260/248 |
| 3,442,977 | 5/1969 | Grabowski | 260/876 |
| 3,442,980 | 5/1969 | Grabowski | 260/880 |
| 3,478,025 | 11/1969 | Kolyer et al. | 260/78 L |
| 3,494,982 | 2/1970 | Grabowski et al. | 260/876 |
| 3,624,252 | 11/1971 | Labarge | 260/248 |
| 3,632,544 | 1/1972 | Boyer | 260/30.4 |
| 3,660,344 | 5/1972 | Michael et al. | 260/37 |
| 3,793,289 | 2/1974 | Koch et al. | 260/45.8 |
| 3,950,306 | 4/1976 | Pews et al. | 260/45.8 |
| 3,959,219 | 5/1976 | Aoyama et al. | 260/45.75 |
| 4,006,114 | 2/1977 | Carlson | 260/45.7 R |

Primary Examiner—Melvyn I. Marquis
Assistant Examiner—R. A. White
Attorney, Agent, or Firm—Joseph O. Shekleton

[57] ABSTRACT

Flame-retardant polymer compositions containing tris(haloarylamino)triazines or tris(haloarylthio)triazines. These triazines impart a high degree of flame retardance to all types of normally flammable polymers but especially to ABS polymers.

13 Claims, No Drawings

FLAME-RETARDANT TRIAZINES

This invention relates as indicated to flame-retardant compositions. More particularly it relates to polymer compositions which have an increased degree of flame retardance because of the presence of certain haloaryl substituted triazines.

Polymers vary widely in their resistance to burning. Some, such as the polyolefins, polystyrene, polyalkyl acrylates and methacrylates, and the like, burn readily. Polytetrafluoroethylene, polyvinylidene chloride and polyvinyl chloride, on the other hand, have a rather high resistance to burning. It is highly desirable that, for certain applications, a polymer should have a high degree of flame retardance so that it will meet various building codes, or that it will meet safety standards imposed on the manufacture of toys, etc.

The treatment of those more flammable polymers to increase their resistance to burning is well known; such treatment in general has involved the incorporation in the polymer composition of substantial proportions of antimony trioxide, halogenated paraffins, halogenated hydrocarbons and low molecular weight phosphate esters. Ordinarily, though, the effective use of these and other additives has required their presence in such high concentrations as to adversely affect the desirable properties of the polymer. Thus, such desirable properties as hardness, clarity, strength, elasticity, etc., are diminished significantly by the presence of large amounts of a flame-retarding chemical.

The formulator's goal, in preparing a flame-retardant polymer composition, is to add just enough of the flame-retardant compound so as to provide the desired degree of flame retardance, but no more than this minimum amount, so as to preserve as much as possible the advantageous properties of the polymer. Frequently, it is not possible to select a flame retardant which will meet these requirements.

Presently used flame-retardant compositions generally include, in addition to the organic flame-retardant compound, a significant proportion, i.e., 1–10%, of an inorganic compound such as antimony trioxide ($Sb_4O_6$), antimony chloride, borax, etc. These inorganic compounds by themselves are relatively ineffective as flame retardants, but act synergistically with the organic flame-retardant compound to give much better results than can be achieved by use of the organic compound alone. By far the most widely used of these inorganic compounds is antimony trioxide; unfortunately, it is relatively expensive, so that its use in large quantities is undesirable. Against this cost factor must be balanced its superior effectiveness as a synergist.

This invention is a polymer composition comprising a normally flammable polymer and a substituted triazine having the structural formula

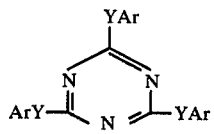

where Ar is haloaryl and Y is S or NH. The halogen contained in such substituted triazines is apparently more efficiently utilized as a flame-retarding agent than the halogen in previously known flame retardants. Also, smaller amounts of inorganic synergist are required.

The halogen of the haloaryl radical preferably is bromine or chlorine. While iodine and fluorine are also contemplated the substituted triazines containing these halogens are not as effective as those which contain bromine or chlorine. Particularly preferred are those substituted triazines wherein each aryl group contains two or more bromine or chlorine atoms. Tribromophenyl-substituted triazines and trichlorophenyl-substituted triazines are specific illustrations of particularly preferred species.

The bridging group between the triazine nucleus and each haloaryl radical is either sulfur (S) or imino (NH). Those triazine compounds wherein the bridging group is sulfur are previously unreported in the prior art, i.e., they are new compounds. Also new are those substituted triazines where the bridging group is imino, and where Ar is either iodo or bromoaryl containing at least three bromine atoms per aryl group.

The relative proportions of the flame-retardant triazines which are to be used in the polymer compositions are, as indicated, the result of a careful balancing of that minimum amount which will provide the desired degree of flame retardance and the maximum amount which will not have too adverse an effect upon the polymer's good properties. In general, it should be present in such concentration as to provide from about 5% to about 20% of halogen in the polymer composition. Most usually, the flame-retardant triazine will be present in such concentration as to provide from about 7% to about 16% of halogen.

As indicated earlier herein, an inorganic synergist usually is used in combination with the triazine. These inorganic synergists include primarily antimony trioxide ($Sb_4O_6$) and sodium borate ($Na_3BO_3$); others include antimony pentoxide ($Sb_2O_5$), antimony chloride ($SbCl_3$), antimony oxychloride ($SbOCl_3$), antimony bromide ($SbBr_3$), arsenic trioxide ($As_2O_3$), arsenic pentoxide ($As_2O_5$), zinc borate ($Zn_3B_4O_9$), stannous oxide hydrate ($SnO \cdot H_2O$), and borax ($Na_2B_4O_7$).

The inorganic synergists, according to one theory, are effective because they react with the halogen-containing flame-retardant triazine to form a volatile metal halide, e.g., $SbBr_3$, which reacts with free radicals produced in the oxidation (burning) reaction and thereby snuffs out the flame.

Although the use of larger amounts of the flame-retardant triazine precludes the necessary use of inorganic synergists, it is preferred in most instances to use a somewhat lesser amount of flame-retardant triazine in combination with an inorganic synergist. The amount of such synergist thus used will range up to about 15% of the polymer compositions. Preferably it will be up to about 10%.

For optimum results the relative proportions of triazine and antimony oxide (as the synergist) should be such that the ratio of halogen (in the triazine) to antimony is about 3:1 on a molar basis.

The triazines of the invention may be prepared from cyanuric chloride.

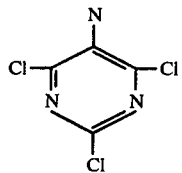

The chlorine atoms above are reactive with the hydrogen of an NH₂ or SH group in a substituted aniline or thiophenyl, to give a substituted triazine. It will be noted that a complete reaction requires three mols of a substituted aniline or thiophenol for each mol of cyanuric chloride. In some instances the reaction proceeds in one step, merely by heating the two reactants, preferably in a solvent such as o-dichlorobenzene, tetrahydrofuran, etc., and in the presence of an alkaline material, e.g., sodium methylate, sodium carbonate, sodium hydroxide, trimethylamine, triethylamine, etc.

In other instances, particularly with certain amino-substituted triazines, it sometimes is advisable to utilize a two-step procedure, forming first the mono- or di-substituted triazine by means of the above reaction conditions, and then forming the desired tri-substituted triazine by treatment under more stringent conditions, viz., heating the intermediate product with a stoichiometric excess of the halo-substituted aromatic amine reactant. In still other instances the desired tri-substituted triazine can be prepared in but one step merely by heating the two reactants at a relatively high temperature, e.g., 100°–200° C, with or without a solvent and without an alkaline material.

In yet another method, the triarylamino-, triarylthio- or triaryloxy-substituted 1,3,5-triazines may be halogenated to yield the corresponding tri(haloaryl) compounds. N,N,′N″-triphenylmelamine, for example, can be chlorinated to produce tri-(chlorophenyl)melamine.

The preparation of illustrative substituted triazines is shown in the following examples.

EXAMPLE I

A mixture of 28.6 g. (0.0824 mol) of 2,4,6-tribromothiophenol, 17.8 g. of a 25% methanol solution of sodium methylate, and 550 ml. of additional methanol is heated at reflux temperature for 0.5 hour, then concentrated to a tan solid by drying in a vacuum oven. This solid is dissolved in 650 ml. of tetrahydrofuran and then treated dropwise, in an atmosphere of nitrogen, with a solution of 5.07 g. (0.0275 mol) of cyanuric chloride in 50 ml. of tetrahydrofuran. The addition of cyanuric chloride is made throughout a period of 30 minutes at room temperature. The resulting mixture then is heated at reflux temperature for six hours, and filtered. The brown filtrate is treated with charcoal and filtered again, then concentrated by means of a flash evaporation. The resulting concentrate is taken up in a small volume of n-heptane and filtered to yield 25.3 of dry, beige solid which is mixed with boiling n-heptane and filtered. The cooled filtrate deposits a solid which is collected on a filter; it weighs 9.1 g. and melts at 235°–238° C. The solid obtained from the boiling n-heptane filtration is treated with charcoal in hot tetrahydrofuran, filtered and the filtrate concentrated and filtered again to yield 77 g. of a tan solid, M.P., 232°–236° C. Both solid fractions are identified by elemental and infrared analyses as 2,4,6-tris(2′,4′,6′-tribromophenylthio-)1,3,5-triazine.

EXAMPLE II

A mixture of 9.4 g. (0.051 mol) of cyanuric chloride, 43.0 g. (0.152 mol) of pentachlorothiophenol, 16.1 g. (0.152 mol) of sodium carbonate and 300 ml. of tetrahydrofuran is prepared and stirred at reflux temperature in a nitrogen atmosphere for 4.5 hours, then filtered. The filtrate is treated with charcoal, then diluted with n-heptane and concentrated by means of flash evaporation to a small volume, then filtered again. The solid is dissolved in 500 ml. of hot toluene, filtered and evaporated to dryness; the solid weighs 28.7 g. M.P., 175°–245° C. Elemental analyses correspond substantially to the theoretical values for 2,4,6-tris-(pentachlorophenylthio-)1,3,5-triazine.

EXAMPLE III

To a solution of 216.0 g. (0.765 mol) of pentachlorothiophenol and 77.4 g. (0.765 mol) of triethylamine in 1500 ml. of tetrahydrofuran, under a nitrogen atmosphere, there is added dropwise at 20°–30° C a solution of 47.0 g (0.255 mol) of cyanuric chloride in 400 ml. of tetrahydrofuran. The addition produces an exothermic reaction and is made over a period of 2.5 hours, after which the mixture is heated at reflux temperature for 7.5 hours. The cooled mixture is filtered and the solid treated with charcoal in 1500 ml. of o-dichlorobenzene and filtered. The filtrate is diluted with xylene and concentrated to a small volume, then taken up in n-heptane. The heptane mixture is filtered to obtain 188.4 g. of a pale yellow solid, M.P., 294°–298° C. Upon purification as in Example II, i.e., by dissolution in xylene, treatment with charcoal, etc., 179.4 g. of a pale yellow solid is obtained, M.P., 318°–320° C. Elemental and infrared analyses, and molecular weight determination, are consistent with the structure of 2,4,6-tris(pentachlorophenylthio-)1,3,5-triazine.

EXAMPLE IV

A mixture of 412.3 g. (1.25 mols) of 2,4,6-tribromoaniline, 226.8 g. (1.25 mols) of cyanuric chloride, 132.5 g. (1.25 mols) of anhydrous, pulverized sodium carbonate and 3.5 liters of xylene is heated at reflux (135° C) for 19.75 hours in a nitrogen atmosphere. The mixture is filtered while hot (at about 135° C), and about 700 ml. of tetrahydrofuran is added during the filtration in order to keep the organic product dissolved during the filtration. The insoluble, off-white solid on the filter (containing mainly inorganic by-products) is discarded. The pale yellow filtrate is treated with activated charcoal, filtered to remove the charcoal, and the filtrate concentrated by distillation at reduced pressure to a small volume. The residue is cooled and filtered to obtain an off-white solid which weighs 350.0 g. after drying to constant weight in a vacuum oven. This intermediate product is identified as 2-(2′,4′,6′-tribromophenylamino)-4,6-dichloro-1,3,5-triazine by its melting point (262°–263.5° C) which is substantially the same as the melting point of another sample of the same intermediate product identified by elemental analyses, molecular weight and infrared spectrum. The yield of this intermediate product is 58.6%.

A solid mixture of 33.5 g. (0.07 mol) of the above 2-(2′,4′,6′-tribromophenylamino-(4,6-dichloro-1,3,5-triazine and 164.9 g. (0.5 mol) of 2,4,6-tribromoaniline is heated with stirring in an oil bath at 150°–184° C for 12 hours. A nitrogen atmosphere is maintained above the reaction mixture. Upon cooling, the mixture is diluted with 400 ml. of boiling tetrahydrofuran and filtered yielding 18.7 g. of a white solid, M.P., 308°–358° C. It is characterized as the desired 2,4,6-tris(2',4',6'-tribromophenylamino-)1,3,5-triazine by elemental analyses.

The tetrahydrofuran filtrate from above is diluted with n-heptane and then concentrated until substantially all of the tetrahydrofuran is removed. Additional n-heptane is added to bring the total volume to 1200 ml.; this mixture is heated to boiling and filtered to obtain a beige crystalline solid which is further purified by charcoal treatment in hot tetrahydrofuran. The 35.3 g of dry solid is mixed with 300 ml. of boiling toluene and filtered to yield an additional 15.6 g. of 2,4,6-tris(2',4',6'-tribromophenylamino-)1,3,5-triazine. The identity as such is indicated by elemental analyses.

EXAMPLE V

A mixture of 92.0 g. (0.42 mol) of p-iodoaniline, 12.9 g. (0.07 mol) of cyanuric chloride and 750 ml. of o-dichlorobenzene is heated in a nitrogen atmosphere at 170°–177° C for 16.5 hours, then filtered. The resulting dark solid is washed with 450 ml. of hot acetone and 6.0 g. of the dried residue is crystallized from o-dichlorobenzene to give a white powdery solid, M.P., 271°–274° C. It is characterized by elemental analyses as 2,4,6-tris(p-iodophenylamino-)1,3,5-triazine.

The rest of the dried residue is washed with 500 ml. of hot tetrahydrofuran to give 35.5 g. of a gray crystalline solid, M.P., 316°–318° C. Elemental analyses indicates it to be a 2:1 mixture of the above 2,4,6-tris(p-iodophenylamino)-1,3,5-triazine and 2,4-bis(p-iodophenylamino-)6-chloro-1,3,5-triazine.

EXAMPLE VI

A mixture of 75.0 g. (0.299 mol) of 2,4-dibromoaniline, 9.2 g. (0.050 mol) of cyanuric chloride and 600 ml. of o-dichlorobenzene is heated at reflux temperature (178° C) under nitrogen, for 20.5 hours. The cooled product mixture is filtered to yield an off-white, crystalline solid, which is washed with 400 ml. of hot tetrahydrofuran to yield 24.5 g. (59.5% of the theory) of a white, crystalline solid, M.P., 305°–7° C. It is dissolved in 600 ml. of hot o-dichlorobenzene, treated with decolorizing charcoal, then filtered and cooled. The cooled filtrate deposits a white, crystalline precipitate which is collected on a filter, M.P., 304°–5° C. Elemental and infrared analyses show it to be the desired 2,4,6-tris(2',4'-dibromophenylamino)-1,3,5-triazine.

EXAMPLE VII

A mixture of 129.1 g. (0.7 mol) of cyanuric chloride, 74.2 g. (0.7 mol) of anhydrous, powdered sodium carbonate, and 800 ml. of xylene is heated with stirring to 85° C in a nitrogen atmosphere. To this stirred mixture there is added dropwise a solution of 137.5 g. (0.7 mol) of 2,4,6-trichloroaniline in 600 ml. of xylene. The addition is completed in 2.5 hours during which time the temperature is 85°–90° C. Then, the mixture is heated for 10 minutes at about 85° C and for 15.3 hours at reflux (138° C). The mixture is filtered while hot to remove the inorganic by-products (74.5 g.). The clear, yellow filtrate is heated with activated charcoal, filtered to remove the charcoal, and the filtrate is concentrated in a flash evaporator to a small volume. The residue is stirred with 400 ml. of n-heptane and filtered to obtain a white, crystalline solid which weighs 173.8 g. after drying in a vacuum oven to constant weight. This solid (M.P., 200°–202° C) is identified as 2-(2',4',6'-trichlorophenylamino-)4,6-dichloro-1,3,5-triazine by means of elemental analyses, molecular weight (in acetone solution), and infrared and nuclear magnetic resonance spectra. The yield is 72.1%.

A solid mixture of 346.3 g. (1.763 mol) of 2,4,6-trichloroaniline and 85.0 g. (0.247 mol) of 2-(2',4',6'-trichlorophenylamino-)4,6-dichloro-1,3,5triazine is heated with stirring, under nitrogen, at 170°–173° C, for 15.5 hours. The product mixture is poured (at 130° C) into 2 liters of n-heptane and filtered while hot, and the crystalline solid washed with another 500 ml. of hot n-heptane. It weighs 131.6 g., M.P. 255°–260° C. Its identity as 2,4,6-tris(2',4',6'-trichlorophenylamino-)1,3,5-triazine is established by elemental analyses.

EXAMPLE VIII

A solution of 279.4 g. (3 mols) of aniline in 850 ml. of tetrahydrofuran is stirred and cooled to 10° C in a nitrogen atmosphere. To this cold solution is added gradually, over a period of 1.75 hours at 10°–15° C, a solution of 92.2 g. (0.5 mol) of cyanuric chloride in 550 ml. of tetrahydrofuran. The mixture is heated at reflux temperature (66° C) for 3 hours, cooled in an ice bath to room temperature, filtered, and the white solid (aniline hydrochloride) is washed with one liter of hot tetrahydrofuran. The combined tetrahydrofuran filtrate and washings are treated with activated charcoal, then diluted with 1 liter of n-heptane and distilled to remove the tetrahydrofuran and most of the heptane. The residue is filtered yielding 159.5 g. of cyanuric trianilide (yield, 90.1%), M.P., 224°–229° C. It is purified by treating with activated charcoal in one liter of hot tetrahydrofuran, diluting with 1 liter of n-heptane, and concentrating to a small volume. The residue is filtered to obtain a pale beige-colored, crystalline solid weighing 120.5 g., M.P., 229°–234° C. Elemental analyses, molecular weight determination (in tetrahydrofuran solution), and infrared spectrum confirm its identify as N,N,'N"-triphenylmelamine ($C_{21}H_{18}N_6$). It can be purified further by crystallization from toluene, M.P., 235.5°–237.5° C.

70.0 g. (0.1975 mol) of the above N,N',N"-triphenylmelamine is mixed with 1.5 liters of glacial acetic acid at room temperature. To this mixture is added 298.3 g. (1.866 mols) of liquid bromine dropwise at 20°–30° C over a period of 85 minutes. After about three quarters of the total amount of bromine is added, a voluminous precipitate forms whereupon an additional 0.7 liters of glacial acetic acid is added, and then the addition of bromine is completed. The resulting mixture is heated at 30°–70° C for two hours and at 70° C for six hours, then filtered, and the pale orange solid washed with 3 liters of demineralized water in three equal portions. The combined acetic acid filtrate and aqueous washings are stored for isolation of the product of Example IX.

The pale orange solid is washed with 1 liter of a mixture of tetrahydrofuran and acetone. The undissolved off-white solid weighs 95.3 g. (yield, 72.0%), M.P., 334°–339° C. It is identified by elemental analyses, and infrared, and nuclear magnetic resonance spectra as 2,4-bis(p-bromophenylamino-)6-(2',4'-dibromophenylamino-)1,3,5-triazine ($C_{21}H_{14}N_6Br_4$).

EXAMPLE IX

The combined acetic acid filtrate and aqueous washings of Example VIII are diluted with an approximately equal volume of cold water. The mixture is filtered to obtain a dark orange, powdery solid weighing 27.0 g., M.P., 262°–278° C. This solid is washed with 400 ml. of a mixture of tetrahydrofuran and acetone. The undissolved residue weighs 9.0 g., M.P. 288°–293° C. It is an off-white, crystalline solid, shown by elemental analyses to be 2-(p-bromophenylamino-)4,6-bis(2',4'-dibromophenylamino-)1,3,5-triazine or $C_{21}H_{13}N_6Br_5$.

The flame retardance of a plastic material can be determined by means of Underwriters Laboratories test UL-94. The test specimen measures 5 inches × 0.5 inch × 0.062 inch; it is suspended vertically at a measured height above the flame from a Bunsen burner. After 10 seconds the flame is removed and the duration of the flaming of the test specimen is noted. Immediately, the flame is placed again under the specimen and after 10 seconds the flame again is withdrawn and the duration of flaming and glowing is noted. Five test specimens are thus tested and the results of all five tests are considered in the determination of a rating for the plastic material.

The following are noted: (1) duration of flaming after first flame application; (2) duration of flaming after second flame application; (3) duration of flaming plus glowing after second flame application; (4) whether or not specimens burn up to their point of suspension; and (5) whether or not specimens drip flaming particles which ignite a cotton swatch placed 12 inches beneath the test specimen. The highest rating given to a material is "V-O". It indicates that (1) no specimen burns with flaming combustion for more than 10 seconds after each application of the test flame; (2) the material does not have a flaming combustion time exceeding 50 seconds for the 10 flame applications for each set of 5 specimens; (3) no specimen burns with flaming or flowing combustion up to the holding clamp; (4) no specimen drips flaming particles that ignite the dry cotton beneath the specimen; and (5) no specimen glows for more than 30 seconds after the second removal of the flame.

The next highest rating is "V-1". It indicates that (1) no specimen burns with flaming combustion for more than 30 seconds after each application of the test flame; (2) the material does not have a flaming combustion time exceeding 250 seconds for the 10 flame applications for each set of 5 specimens; (3) no specimen burns with flaming or flowing combustion up to the holding clamp; (4) no specimen drips flaming particles that ignite the dry cotton beneath the specimen; and (5) no specimen glows for more than 60 seconds after the second removal of the flame.

The lowest rating given to a material in this test is "NSE" ("non-self-extinguishing"). It indicates that the material has failed to meet one or more of the criteria for the UL-94 vertical test.

Another test for the flammability of a plastic material measures the minimum concentration of oxygen that will just support combustion. The test is an ASTM test, D 2863-70. It is carried out in a glass column wherein the concentration of oxygen is varied until that concentration is found which will just support the burning of a test specimen, for 3 minutes or until 50 mm of the specimen has burned. The test specimen is 70–150 mm long by 6.5 mm wide by 3.0 mm thick. This concentration of oxygen is called the oxygen index. A high oxygen index indicates a highly flame retardant specimen.

A formulation of flame-retardant polymeric compositions based on the substituted triazines herein is shown in Table I.

TABLE I

|  | Ex. I | Ex. II | Ex. III | Ex. IV | Ex. VI |
|---|---|---|---|---|---|
| ABS[a] | 70.00 | 80.00 | 100.00 | 100.00 | 100.00 |

TABLE I-continued

|  | Ex. I | Ex. II | Ex. III | Ex. IV | Ex. VI |
|---|---|---|---|---|---|
| CPE[b] | 3.50 | 4.00 | 5.00 | 5.00 | 5.00 |
| $Sb_4O_6$ | 5.25 | 12.00 | 10.70 | 7.70 | 7.90 |
|  | (4.6% Sb) | (8.1% Sb) | (6.0% Sb) | (4.6% Sb) | (4.6% Sb) |
| Mg Stearate | 0.525 | 0.60 | 0.75 | 0.75 | 0.75 |
| Dibutyl Tin Maleate | 0.875 | 1.00 | 1.25 | 1.25 | 1.25 |
| Polyethylene Glycol | 0.175 | 0.20 | 0.50 | 0.50 | 0.50 |
| Sample of Flame Retardant | 15.80 | 26.30 | 31.10 | 24.70 | 27.90 |
|  | (10.5% Br) | (12.2% Cl) | (12.0% Cl) | (11.5% Br) | (11.3% Br) |

[a]A graft polymer of 51.5% of styrene and 28.5% of acrylonitrile on 20% of polybutadiene.
[b]Chlorinated polyethylene containing 36% chlorine.

The "sample of flame retardant" in each case above (TABLE I) is the product obtained by the procedure of the indicated example.

The flame retardant properties of these compositions are shown by the data set out in TABLE II.

TABLE II

| Sample | Rating | MBT* | ABT* | O.I.* |
|---|---|---|---|---|
| Ex. I | V-O | 2 sec. | 1.1 sec. | — |
| Ex. II | V-O | 3 sec. | 2.2 sec. | — |
| Ex. III | V-O | 2 sec. | 0.9 sec. | 25.5 |
| Ex. IV | V-O | 1 sec. | 0.3 sec. | 30.5 |
| Ex. VI | V-O | 2 sec. | 0.9 sec. | 29.5 |

MBT* - maximum burn time after removal of the ignition source;
ABT = average burn time after removal of the ignition source;
O.I. = oxygen index.

The effectiveness of 2,4,6-tris-(pentachlorophenylthio-)1,3,5-triazine, prepared as in Example III, in varying concentrations and in varying ratios of concentrations with respect to the concentration of antimony oxide, is shown in TABLE III which shows the various compositions and test data resulting from testing those compositions. In each case the composition is identical to that of "Ex. III" of TABLE I except for the amounts of "Sample" and "$Sb_4O_6$".

TABLE III

| Amounts | | | | | |
|---|---|---|---|---|---|
| Sample | $Sb_4O_6$ | Rating | MBT | ABT | O.I. |
| 30.1 | 6.9 | V-O | 2 | 1.3 | 25.5 |
| 29.1 | 3.3 | V-O | 7 | 2.5 | 25.5 |
| 24.3 | 8.4 | NSE[d] | — | | 26.0 |
| 18.3 | 6.3 | NSE | — | | 25.0 |
| 13.0 | 4.5 | NSE | — | | 26.5 |

[d]Not self-extinguishing.

Comparative test data showing the relative effectiveness of the substituted triazines of this invention and those (oxygen analogs) of the prior art are presented in TABLE V. In each case the polymer composition contains the following components:

| Parts | Components |
|---|---|
| 100 | ABS |
| 5.0 | CPE |
| 0.75 | Mg Stearate |
| 1.25 | Dibutyl Tin Dimaleate |
| 0.50 | Polyethylene Glycol | plus, of course, the substituted triazine and, in most cases, antimony trioxide. The compositions of the triazines (shown in TABLE IV) conform to the formula

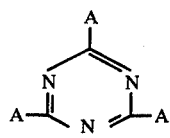

the structure of A being indicated in TABLE IV; the number immediately following the indicated structure designates the amount of the triazine characterized by such structure.

TABLE IV

| No. | A (parts) | % Halogen | $Sb_4O_6$ (parts) | % Sb |
|---|---|---|---|---|
| 1. | 2,4,6-$Br_3C_6H_2O$-(33.5) | 16 | 0 | 0 |
| 2. | 2,4,6-$Br_3C_6H_2NH$-(33.3) | 16 | 0 | 0 |
| 3. | 2,4,6-$Br_3C_6H_2O$-(13.0) | 7 | 7.7 | 5 |
| 4. | 2,4,6-$Br_3C_6H_2S$-(14.0) | 7 | 7.7 | 5 |
| 5. | 2,4,6-$Cl_3C_6H_2O$-(30.8) | 10 | 8.8 | 5 |
| 6. | 2,4,6-$Cl_3C_6H_2NH$-(30.6) | 10 | 8.8 | 5 |
| 7. | $Cl_5C_6O$-(29.0) | 12 | 10.6 | 6 |
| 8. | $Cl_5C_6S$-(31.1) | 12 | 10.7 | 6 |

TABLE V

| No. | UL 94 Rating | ABT | MBT | O.I. |
|---|---|---|---|---|
| 1. | V-1 | 7.0 | 19 | 24.5 |
| 2. | V-1 | 4.1 | 12 | 25.0 |
| 3. | V-O | 0.9 | 2 | 26.0 |
| 4. | V-O | 1.1 | 3 | 27.5 |
| 5. | NSE | — | — | 24.5 |
| 6. | V-1 | 8.1 | 15 | 27.5 |
| 7. | V-O | 2.7 | 5 | 25.5 |
| 8. | V-O | 0.9 | 2 | 25.5 |

It will be noted, in each comparison, that the imino-containing and sulfur-containing triazines are usually superior and at least equal to the oxygen-containing analogs with respect to flame-retardant properties.

All parts and percentages herein are by weight unless otherwise expressly stated.

The triazine derivatives of Examples V and VIII are also tested in polymeric compositions by similar methods as above, and flame retardance improvements are observed.

I claim:

1. A compound having the structural formula:

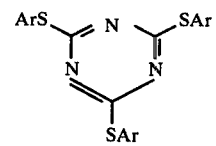

where Ar is the same or different polybromoaryl carbocyclic radical.

2. A compound of claim 1 wherein Ar is polybromophenyl.

3. A compound of claim 1 wherein Ar is tribromophenyl.

4. A compound having the structural formula:

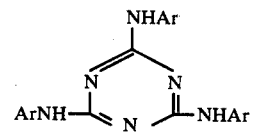

where Ar is the same or different carbocyclic polybromoaryl radical containing at least three bromine atoms per carbocyclic radical.

5. A polymer composition comprising an ABS graft copolymer and a substituted triazine having the structural formula

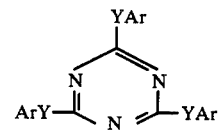

where Ar is the same or different bromoaryl or chloroaryl carbocyclic radical and Y is S or NH, with the proviso that Ar is not chloroacyl when Y is S.

6. The polymer composition of claim 5 wherein Ar is polybromoaryl carbocyclic.

7. The polymer composition of claim 5 wherein Ar is tribromoaryl carbocyclic.

8. The polymer composition of claim 5 wherein Y is NH.

9. The polymer composition of claim 8 wherein Ar is chloroaryl carbocyclic.

10. The polymer composition of claim 9 wherein Ar is trichloroaryl carbocyclic.

11. The polymer composition of claim 5 wherein Y is S.

12. The polymer composition of claim 11 wherein Ar is bromoaryl carbocyclic.

13. The polymer composition of claim 12 wherein Ar is polybromoaryl carbocyclic.

* * * * *